United States Patent
Ailinger

(10) Patent No.: US 11,589,732 B2
(45) Date of Patent: Feb. 28, 2023

(54) COVER MEMBER FOR ROLLER OF ENDOSCOPE APPARATUS AND METHOD OF PROCESSING ENDOSCOPE APPARATUS

(71) Applicant: OLYMPUS CORPORATION, Tokyo (JP)

(72) Inventor: Robert E. Ailinger, Norwood, MA (US)

(73) Assignee: OLYMPUS CORPORATION, Tokyo (JP)

( * ) Notice: Subject to any disclaimer, the term of this patent is extended or adjusted under 35 U.S.C. 154(b) by 524 days.

(21) Appl. No.: 16/587,891

(22) Filed: Sep. 30, 2019

(65) Prior Publication Data

US 2021/0093161 A1    Apr. 1, 2021

(51) Int. Cl.
*A61B 1/00*      (2006.01)
*G01K 11/12*   (2021.01)

(52) U.S. Cl.
CPC ........ *A61B 1/00071* (2013.01); *A61B 1/0014* (2013.01); *A61B 1/00133* (2013.01); *G01K 11/12* (2013.01)

(58) Field of Classification Search
CPC ............ A61B 1/00071; A61B 1/00087; A61B 1/0016; A61B 1/00133; A61B 1/0014; A61B 1/00131; A61B 1/00135; A61B 1/00142; A61B 1/00151; A61B 1/00154; A61B 1/00156; A61B 1/121–123; A61B 1/125; G01K 11/12; G01K 17/00
See application file for complete search history.

(56) References Cited

U.S. PATENT DOCUMENTS 8,353,817 B2 *    1/2013   Ziegler ............. A61M 25/0116
                                                                  73/865.8
2005/0075555 A1    4/2005   Glukhovsky et al.
(Continued)

FOREIGN PATENT DOCUMENTS

JP         3542208 B2 *   7/2004
JP         2008-86574    *   4/2008   ............... A61B 1/00

OTHER PUBLICATIONS

International Search Report dated Dec. 15, 2020 together with the Written Opinion received in International Application No. PCT/JP2020/036954.

*Primary Examiner* — Ryan N Henderson
*Assistant Examiner* — Megan Elizabeth Monahan
(74) *Attorney, Agent, or Firm* — Scully, Scott, Murphy & Presser, P.C.

(57) ABSTRACT

An endoscope apparatus having: an insertion portion extending along a longitudinal axis; a roller driven by a drive force to rotate around the longitudinal axis; and a cover member covering the roller, wherein the cover member has: a base layer having: an outer surface direction side; and an inner surface direction side arranged to contact the roller, wherein portions of the base layer covering the roller as the roller rotates around the longitudinal axis of the insertion portion elastically elongate in an outer surface direction of the insertion portion, and wherein the base layer has a secondary material being a first color at a first temperature range and a second color at a second temperature range; and an external coating layer formed on at least one of the outer surface direction side and the inner surface direction side of the base layer.

12 Claims, 8 Drawing Sheets

(56) References Cited

U.S. PATENT DOCUMENTS

2013/0165856 A1\* 6/2013 Frassica .................. A61B 1/04
 604/95.01
2014/0330079 A1 11/2014 Ishizaki et al.
2017/0059009 A1\* 3/2017 Ishizaki ................... F16H 7/02

\* cited by examiner

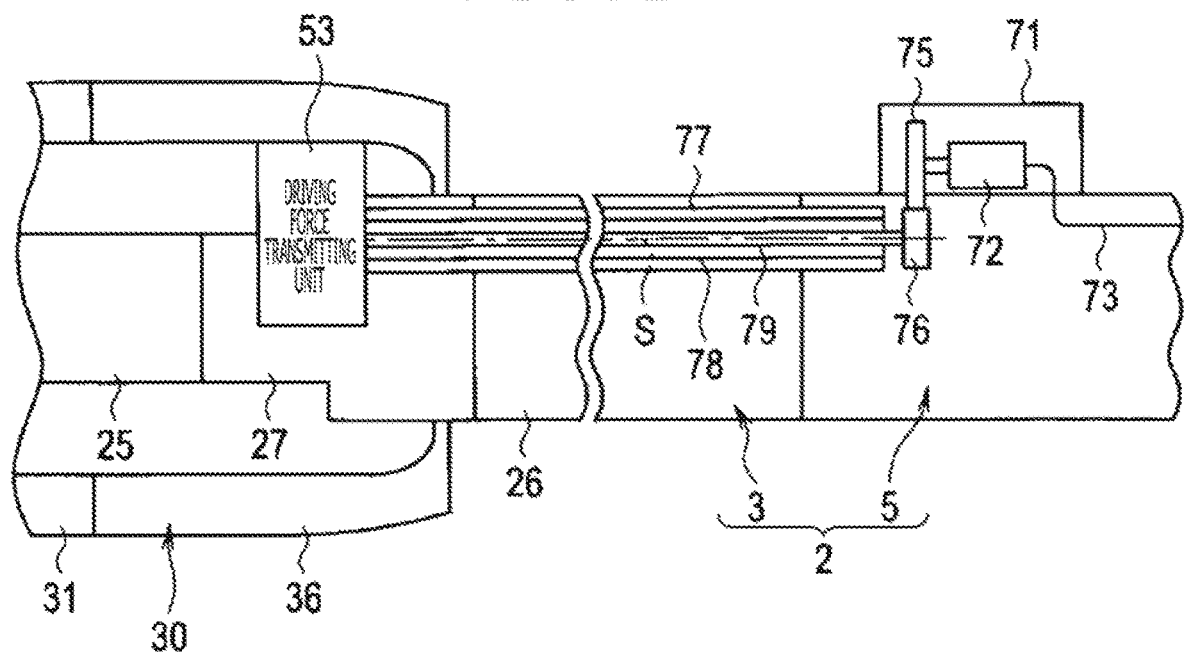
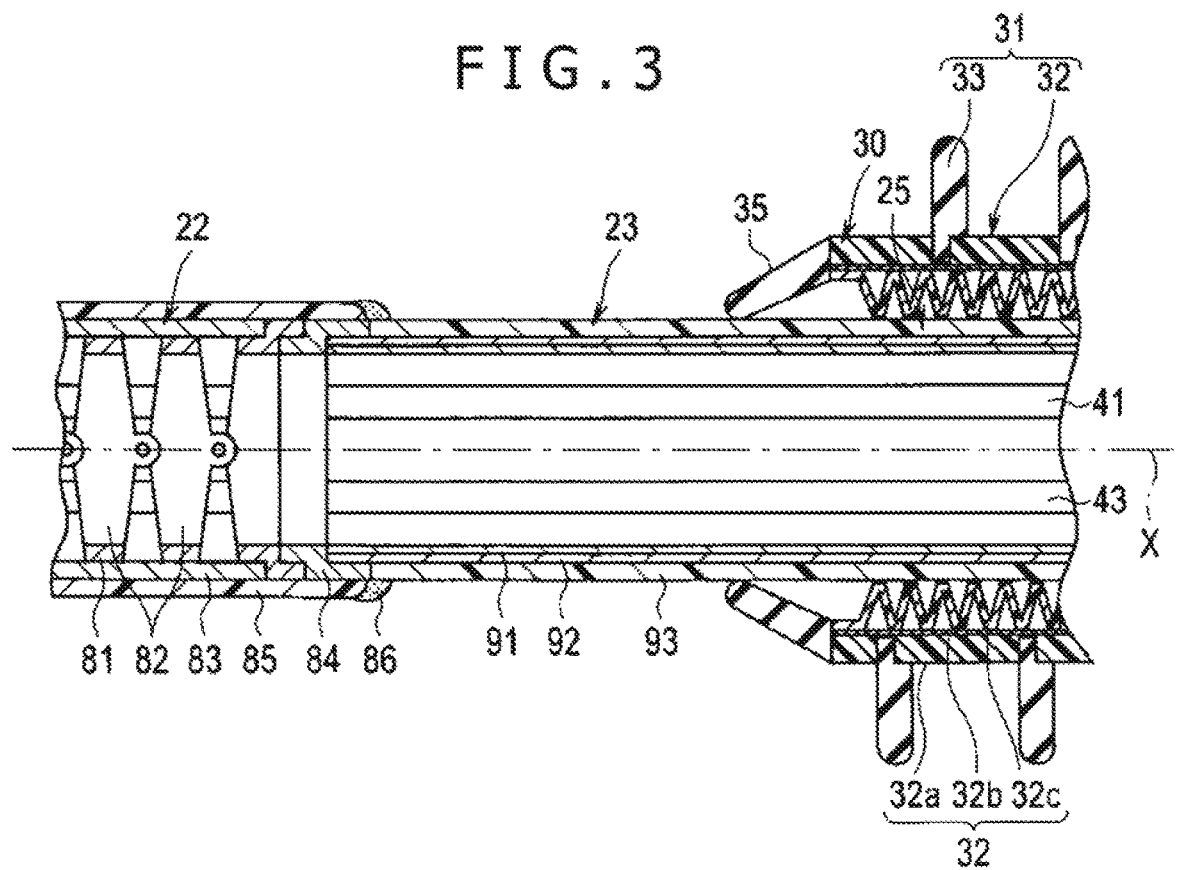

FIG. 8
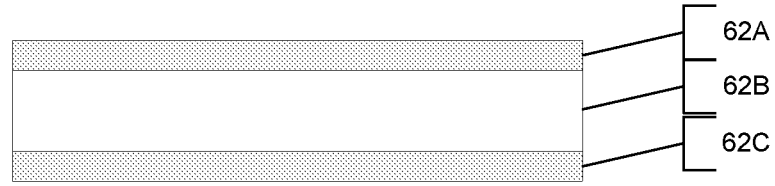
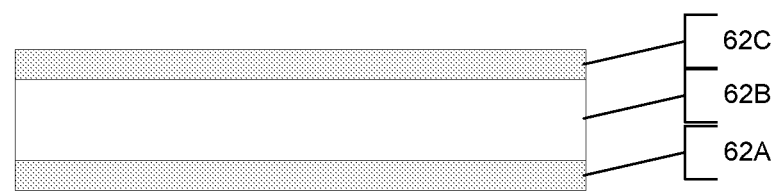
FIG. 9
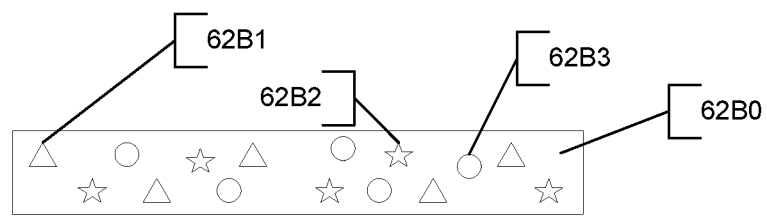
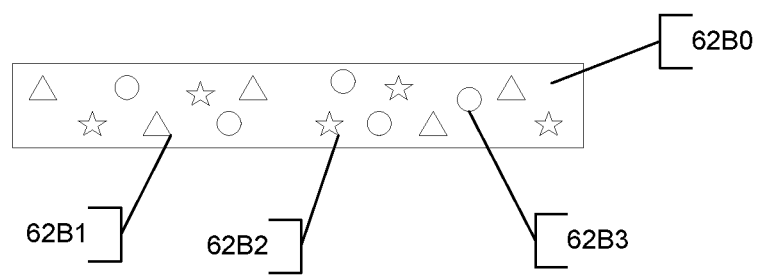

FIG. 10
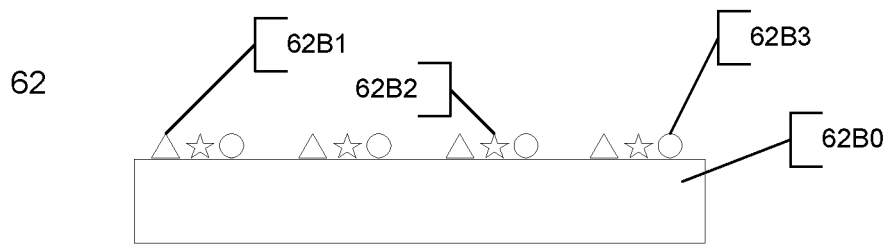
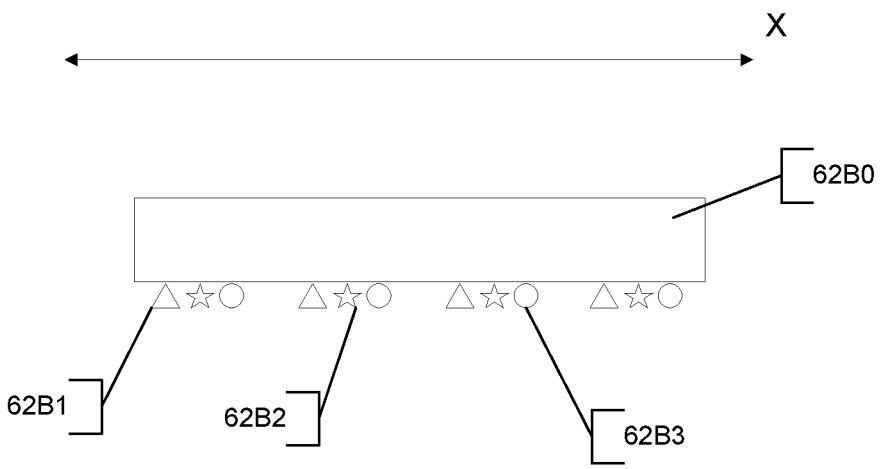
FIG. 11
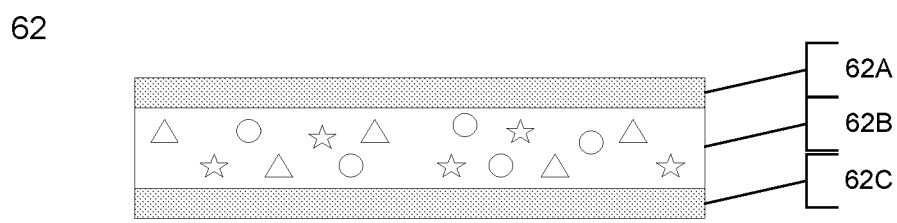
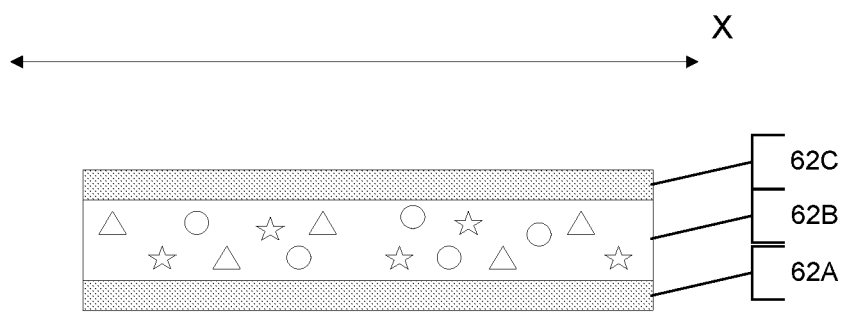

COVER MEMBER FOR ROLLER OF ENDOSCOPE APPARATUS AND METHOD OF PROCESSING ENDOSCOPE APPARATUS

BACKGROUND

Field of the Invention

An insertion device such as an endoscope apparatus can have an insertion portion that is elongated in shape and is bendable. The insertion device can further have an assist tool attachable to and rotatable by portions of the insertion portion.

Description of Related Art

A need is recognized to improve the structures for transmitting driving force from the insertion portion to the assist tool. Further, a need is recognized for a technique to confirm with higher certainty that the insertion portion is successfully cleaned, disinfected, and sterilized in a process for reprocessing the insertion portion. Still further, a need is recognized for a technique to confirm with higher certainty that the insertion portion is manufactured by an original manufacturer.

SUMMARY

In one embodiment of the present invention, there is provided an endoscope apparatus comprising: an insertion portion extending along a longitudinal axis; a roller configured to be driven by a drive force to rotate around the longitudinal axis of the insertion portion; and a cover member configured to be attached to the insertion portion to cover the roller, wherein the cover member comprises: a base layer having: an outer surface direction side; and an inner surface direction side arranged to contact the roller, wherein portions of the base layer covering the roller as the roller rotates around the longitudinal axis of the insertion portion are configured to be elastically elongated in an outer surface direction of the insertion portion; and an external coating layer formed on at least one of the outer surface direction side and the inner surface direction side of the base layer.

In another embodiment, there is provided an endoscope apparatus comprising: an insertion portion extending along a longitudinal axis; and a cover member configured to cover at least a portion of the insertion portion, wherein the cover member comprises: a base layer comprising: an elastomer; and one or more secondary materials configured to change color in response to temperature change of the one or more secondary materials.

In another embodiment, there is provided a method of processing an endoscope apparatus, wherein the endoscope apparatus comprises: an insertion portion extending along a longitudinal axis; a roller configured to be driven by a drive force to rotate around the longitudinal axis of the insertion portion; and a cover member configured to be attached to the insertion portion to cover the roller, wherein the cover member comprises: a base layer, wherein portions of the base layer covering the roller as the roller rotates around the longitudinal axis of the insertion portion are configured to be elastically elongated in an outer surface direction of the insertion portion, and wherein the base layer comprises: an elastomer; and a secondary material configured to change color in response to temperature change of the secondary material from a first temperature associated with a first temperature of the elastomer having a higher coefficient of friction to a second temperature associated with a second temperature of the elastomer having a lower coefficient of friction, and wherein the method comprises: performing inspection of the cover member to determine whether the secondary material has undergone the change in color; in response to determining that the secondary material has not undergone the change in color, performing warming the cover member; repeating performance of the inspection of the cover member and the warming of the cover member until determining that the secondary material has undergone the change in color; and in response to determining that the secondary material has undergone the change in color, attaching a rotating unit having a tubular shape to the insertion portion at a position where the drive force is transmitted from the roller to the rotating unit via the cover member.

BRIEF DESCRIPTION OF THE SEVERAL VIEWS OF THE DRAWINGS

The accompanying drawings illustrate embodiments of the invention, and together with the general description given above and the detailed description of the embodiments given below, serve to explain the various aspects of the present invention.

FIG. 2 is a diagram depicting a configuration that transmits a rotational driving force to a rotating unit according to the one aspect of the present disclosure.

FIG. 3 is a diagram depicting the configuration of a bending part, a first flexible tube part, a second flexible tube part, and the rotating unit according to the one aspect of the present disclosure.

FIG. 8 is a section view of the cover member according to one aspect of the present disclosure.

FIG. 9 is a section view of the cover member according to one aspect of the present disclosure.

FIG. 10 is a section view of the cover member according to one aspect of the present disclosure.

FIG. 11 is a section view of the cover member according to one aspect of the present disclosure.

DETAILED DESCRIPTION

Figure 1:
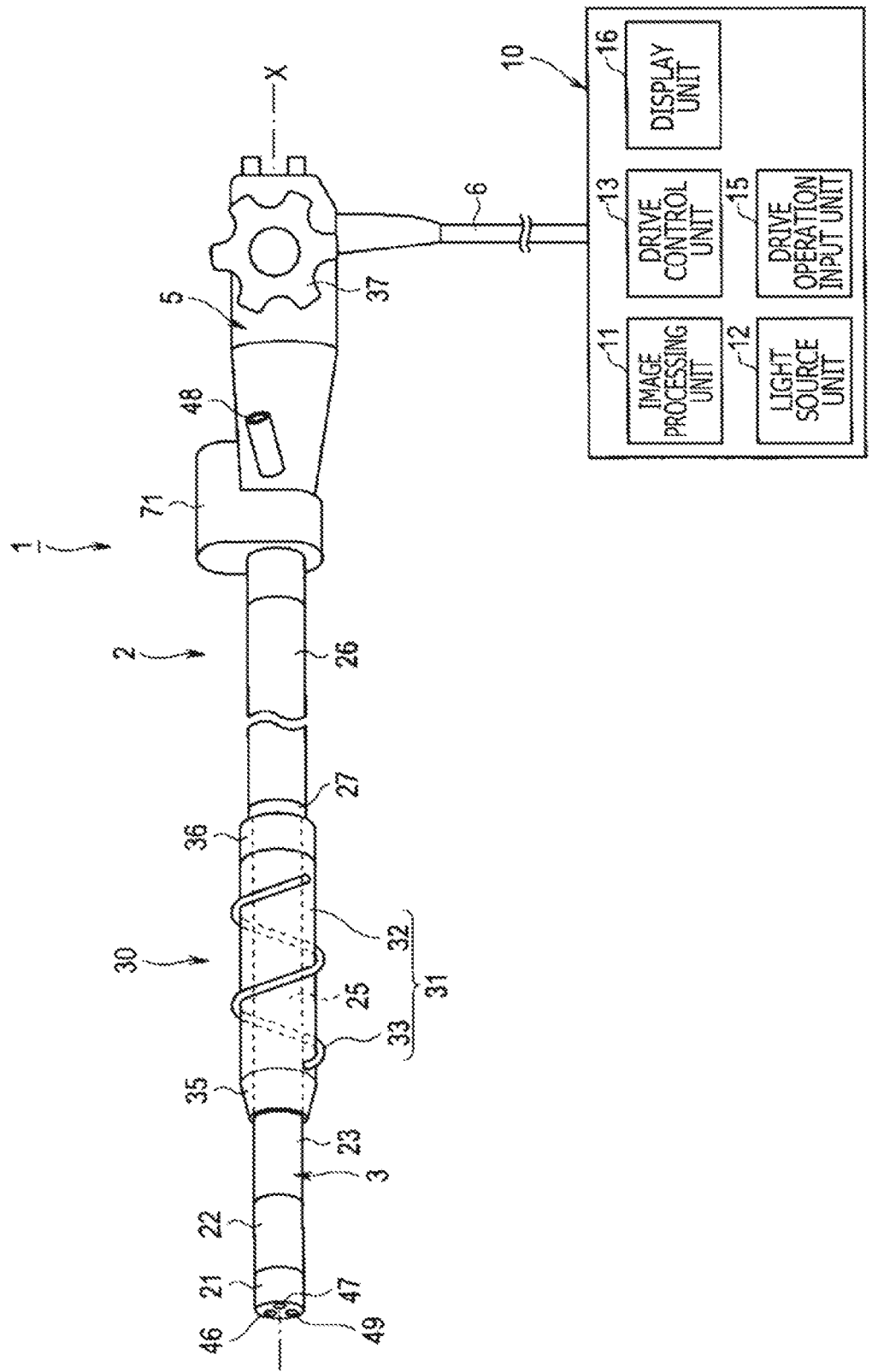
FIG. 1 is a diagram depicting an endoscope apparatus that is an insertion apparatus according to one aspect of the present disclosure.

Hereinafter, embodiments of the present invention will be described with reference to the accompanying drawings.

In the respective diagrams used for the following description, constituent elements whose scale is made different on each constituent element basis also exist in order to cause each constituent element to have such a size as to be recognizable on the drawing. That is, the present disclosure is not limited to only the numbers of constituent elements, the shapes of constituent elements, the ratio of the sizes of constituent elements, and the relative positional relationship among the respective constituent elements described in these diagrams.

In one embodiment of the present invention, there is provided an insertion device having an insertion section that is elongated in shape and is bendable. An endoscope apparatus 1 that is suitable for medical procedures will be described as an example of the insertion device. The insertion device is, however, not limited to an endoscope apparatus for medical procedures and may encompass other endoscope apparatuses suitable for other purposes, such as an endoscope apparatus that is suitable for industrial applications. The endoscope apparatus 1 may, but is not required, to include an illumination optical system, an observation optical system, or one or more sensors (e.g., one or more image sensors) included in some conventional endoscopes. Other insertion devices other than endoscope apparatus are also contemplated. For example, an insertion device having an insertion portion, such as a catheter is also within the scope of the present invention.

As depicted in FIG. 1, the endoscope apparatus 1 can extend along a longitudinal axis X. The endoscope apparatus 1 can include an endoscope 2. The endoscope 2 can include an insertion portion 3, an operation unit 5, and a peripheral unit 10. Description will be made below in such a manner that the extension side of the insertion portion 3 as one side of a direction parallel to the longitudinal axis X of the endoscope 2 is defined as the distal direction and the side of the operation unit 5 in the opposite direction to the distal direction is defined as the proximal direction. Furthermore, the distal direction and the proximal direction are axis-parallel directions parallel to the longitudinal axis X.

The peripheral unit 10 can include an image processing unit 11 such as an image processor such as one or more central processing units (CPUs), a light source unit 12 that can include a light source such as a lamp, a drive control unit 13 that can include a power supply, a storing unit such as a memory, and a CPU or an application-specific integrated circuit (ASIC) for example, a drive operation input unit 15 that can include buttons, foot switches, and so forth, and a display unit 16 such as a monitor.

The insertion portion 3 of the endoscope 2 can be extended along the longitudinal axis X and can be inserted into a cavity (e.g., a body cavity) at the time of use of the endoscope apparatus 1. The insertion portion 3 can include a distal end forming part 21 that forms the distal end of the insertion portion 3, a bending part 22 provided on the proximal direction side relative to the distal end forming part 21, a first flexible tube part 23 provided on the proximal direction side relative to the bending part 22, a second flexible tube part 25 provided on the proximal direction side relative to the first flexible tube part 23, and a third flexible tube part 26 provided on the proximal direction side relative to the second flexible tube part 25.

A base part 27 can be provided between the second flexible tube part 25 and the third flexible tube part 26 along the axis-parallel direction parallel to the longitudinal axis X. The second flexible tube part 25 can be joined to the third flexible tube part 26 with the intermediary of the base part 27.

Here, in the section orthogonal to the longitudinal axis X, such a direction as to get further away from the longitudinal axis X is defined as the outer surface direction, or axis-separated direction, and the central direction toward the longitudinal axis X is defined as the inner surface direction, or axis-oriented direction.

In the insertion portion 3, a rotating unit 30 (also referred to as an assist tool) that has a tubular shape and is of a disposable or expendable type can be provided on the outer surface direction side. That is, in the state in which the insertion portion 3 is inserted in the rotating unit 30, this rotating unit 30 can be mounted to the second flexible tube part 25.

In the endoscope 2, in the state in which the rotating unit 30 is mounted to the insertion portion 3, the rotating unit 30 can rotate around the longitudinal axis X relative to the insertion portion 3 by transmission of a rotational driving force thereto.

The rotating unit 30 can include a spiral tube 31 extended along the longitudinal axis X. The spiral tube 31 can include a tube part 32 and a fin part 33 extended on the outer circumferential surface of this tube part 32. The configuration of this tube part 32 will be described in detail later. In the spiral tube 31, the tube part 32 may by a corrugated tube.

The fin part 33 can extend from the proximal direction side to the distal direction side with a helical shape, with the longitudinal axis X being the center. A distal-side tubular part 35 can be provided on the distal direction side of the spiral tube 31 in the rotating unit 30.

The distal-side tubular part 35 can be formed into a tapered shape in which the outer diameter becomes smaller as the position gets closer to the distal direction side. Furthermore, a proximal-side tubular part 36 with a tubular shape can be provided on the proximal direction side of the spiral tube 31.

In the state in which the fin part 33 of the spiral tube 31 is pressed in the inner surface direction by a body cavity wall or the like, the rotating unit 30 can rotate around the longitudinal axis X. Thereby, a propulsive force in the distal direction or the proximal direction can act on the insertion portion 3 and the rotating unit 30.

Specifically, the movability in the insertion direction of the insertion portion 3, or distal direction, in a cavity (e.g., a body cavity such as inside of a small intestine or inside of a large intestine) is improved due to the propulsive force in the distal direction, and the movability in the withdrawal direction of the insertion portion 3, or proximal direction, in the cavity is improved due to the propulsive force in the proximal direction.

One end of a universal cord 6 can be connected to the operation unit 5 of the endoscope 2. The other end of the universal cord 6 can be connected to the peripheral unit 10. On the outer surface of the operation unit 5, a bending operation knob 37 to which bending operation of the bending part 22 is input can be provided.

Furthermore, a procedure instrument insertion part 48 into which a procedure instrument, such as a pair of forceps, can be inserted, can be provided on the outer surface of the operation unit 5. This procedure instrument insertion part 48 can communicate with a channel tube 43 (see FIG. 3) disposed in the insertion portion 3.

Specifically, the channel tube 43 can pass through the inside of the insertion portion 3 and the inside of the operation unit 5 and one end thereof can be connected to the procedure instrument insertion part 48. Furthermore, the procedure instrument inserted from the procedure instrument insertion part 48 can pass through the inside of the channel tube 43 and can protrude in the distal direction from an opening 49 of the distal end forming part 21. Then, procedure by the procedure instrument can be carried out in the state in which the procedure instrument protrudes from the opening 49 of the distal end forming part 21.

A motor housing 71 can be joined to the operation unit 5. An electric motor 72 (see FIG. 2) that is a drive source can be housed inside the motor housing 71.

As depicted in FIG. 2, one end of a motor cable 73 can be connected to the electric motor 72 housed in the motor housing 71 provided on the operation unit 5. The motor cable 73 can be extended to pass through the inside of the operation unit 5 and the inside of the universal cord 6 and the other end thereof can be connected to the drive control unit 13 of the peripheral unit 10.

The electric motor 72 can be driven by being supplied with power from the drive control unit 13 through the motor cable 73. Furthermore, due to the driving of the electric motor 72, a rotational driving force that rotates the rotating unit 30 can be generated. A relay gear 75 can be attached to the electric motor 72. Moreover, a drive gear 76 that meshes with the relay gear 75 can be provided inside the operation unit 5.

As depicted in FIG. 3, inside the insertion portion 3, an imaging cable 41, a light guide 42, and the above-described channel tube 43 can extend along the longitudinal axis X.

Furthermore, the bending part 22 of the insertion portion 3 can include a bending tube 81. This bending tube 81 can include plural bending pieces 82 made of metal.

Each of the plural bending pieces 82 can be pivotally joined to an adjacent one of the plural bending pieces 82. In the bending part 22, the outer surface direction side of the bending tube 81 can be covered by a bending reticular tube 83 that can be a bending blade. In the bending reticular tube 83, wires (not depicted) made of a metal can be woven into a mesh shape. Moreover, in the bending part 22, the outer surface direction side of the bending reticular tube 83 can be covered by a bending envelope 85. The bending envelope 85 can be formed of, for example, fluorine rubber.

An imaging element (not depicted) that images a subject can be provided inside the distal end forming part 21, or distal part, of the insertion portion 3. This imaging element can carry out imaging of a subject through an observation window 46 that is depicted in FIG. 1 and can be provided at the distal end forming part 21 of the endoscope 2.

One end of the imaging cable 41 can be connected to the imaging element. The imaging cable 41 can extend to pass through the inside of the insertion portion 3, the inside of the operation unit 5, and the inside of the universal cord 6 and the other end thereof can be connected to the image processing unit 11 of the peripheral unit 10 depicted in FIG. 1.

Image processing of a subject image obtained by the imaging can be executed by the image processing unit 11, so that an image of the subject is generated. Then, the generated image of the subject can be displayed on the display unit 16 (see FIG. 1).

Furthermore, the light guide 42 can extend to pass through the inside of the insertion portion 3, the inside of the operation unit 5, and the inside of the universal cord 6 and can be connected to the light source unit 12 of the peripheral unit 10. Light emitted from the light source unit 12 can be guided by the light guide 42 and a subject can be irradiated with the light from an illumination window 47 at the distal part, or distal end forming part 21, of the insertion portion 3 depicted in FIG. 1.

Figure 4:
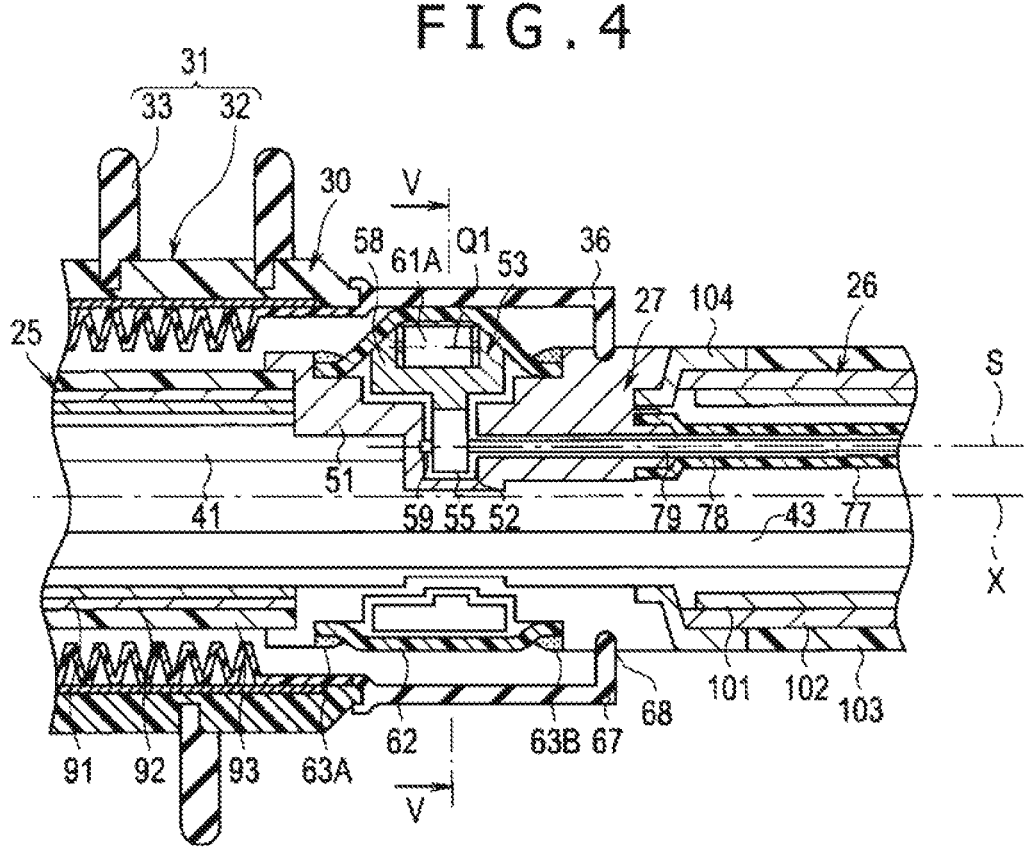
FIG. 4 is a diagram depicting the configuration of the second flexible tube part, a third flexible tube part, a base part, and the rotating unit according to the one aspect of the present disclosure.

As depicted in FIG. 4, at the base part 27, a support member 51 formed from a metal can be provided. The proximal part of the second flexible tube part 25 can be joined to the distal part of the support member 51.

Furthermore, the distal part of the third flexible tube part 26 can be joined to the proximal part of the support member 51. Due to this, the second flexible tube part 25 and the third flexible tube part 26 can be connected via the base part 27.

Figure 5:
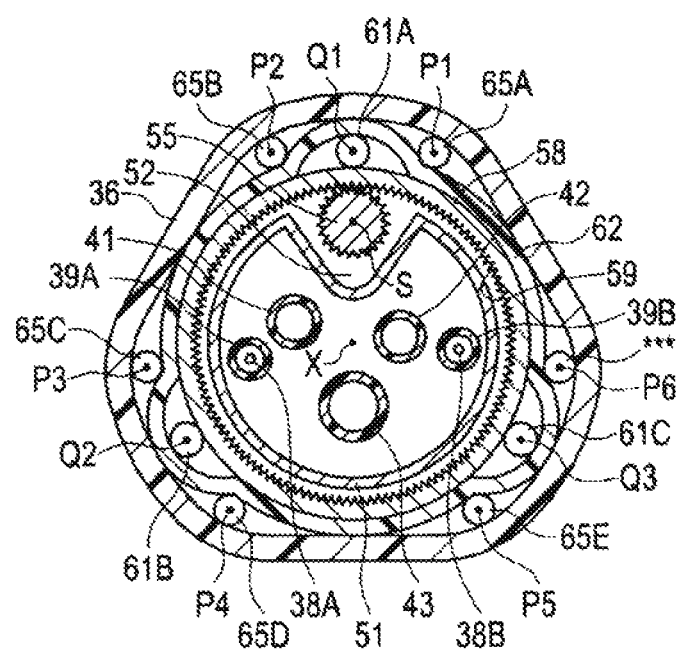
FIG. 5 is a sectional view along line V-V in FIG. 4 according to the one aspect of the present disclosure.

As depicted in FIG. 4 and FIG. 5, a hollow part 52 can be defined by the support member 51 in the base part 27. Furthermore, a driving force transmitting unit 53 can be attached to the support member 51.

The driving force transmitting unit 53 can be disposed in the hollow part 52. Furthermore, a rotational driving force that rotates the rotating unit 30 can be transmitted to the driving force transmitting unit 53 and thereby the driving force transmitting unit 53 can be driven.

The driving force transmitting unit 53 can include a drive gear 55. Moreover, the driving force transmitting unit 53 can include a rotating tubular member 58. The rotating tubular member 58 can be attached to the base part 27 in the state in which the support member 51 is inserted in the rotating tubular member 58. The rotating tubular member 58 can rotate around the longitudinal axis X relative to the insertion portion 3, or the base part 27.

Here, the two directions in which the rotating unit 30 rotates are defined as the direction around the longitudinal axis X. On the inner circumferential surface of the rotating tubular member 58, an inner circumferential gear part 59 can be provided across the whole circumference regarding the direction around the longitudinal axis X. The inner circumferential gear part 59 can mesh with the drive gear 55.

In the present embodiment, three inside rollers 61A to 61C can be attached to the rotating tubular member 58. Although a description of three inside rollers is provided, few or more inside rollers can be provided. The inside rollers 61A to 61C can each be disposed separately from each other by a predetermined interval in the direction around the longitudinal axis X.

The respective inside rollers 61A to 61C have corresponding roller axes Q1 to Q3. The respective inside rollers 61A to 61C can freely rotate relative to the rotating tubular member 58, with the corresponding roller axes Q1 to Q3 being the center.

Furthermore, the inside rollers 61A to 61C can each freely rotate integrally with the rotating tubular member 58 around the longitudinal axis relative to the insertion portion 3, or the base part 27.

The outer surface direction side of the rotating tubular member 58 and the inside rollers 61A to 61C can be covered by a cover member 62 with a tubular shape. The distal end of the cover member 62 can be attached (e.g., fixed) to the outer circumferential surface of the support member 51 with the intermediary of a bonding part 63A such as an adhesive and the proximal end of the cover member 62 can be attached (e.g., fixed) to the outer circumferential surface of the support member 51 with the intermediary of a bonding part 63B such as an adhesive. Each of the bonding part 63A and the bonding part 63B can alternatively include a thread-like member wrapped around and compressing the corresponding ends of the cover member 62 and an adhesive provided on the thread-like member.

By the cover member 62, the hollow part 52 in which the driving force transmitting unit 53 is disposed can be separated from the outside of the insertion portion 3. At the attachment position of the distal end of the cover member 62 and the attachment position of the proximal end of the cover member 62, watertightness between the support member 51 and the cover member 62 can be maintained.

Due to this, the flow of a liquid from the outside of the insertion portion 3 into the hollow part 52 and the driving force transmitting unit 53 can be reduced. Furthermore, at the sites at which the inside rollers 61A to 61C are located, the cover member 62 can protrude in the outer surface direction in the direction around the longitudinal axis X.

The cover member 62 can be attached (e.g., fixed) to the insertion portion 3 and the rotating tubular member 58 and the inside rollers 61A to 61C can each rotate around the longitudinal axis X relative to the cover member 62.

As depicted in FIG. 5, six outside rollers 65A to 65F can be attached to the inner circumferential surface of the proximal-side tubular part 36. The outside rollers 65A to 65F can be located on the outer surface direction side of the cover member 62.

In the state in which the rotating unit 30 is mounted to the insertion portion 3, in the direction around the longitudinal axis X, the inside roller 61A can be located between the outside roller 65A and the outside roller 65B, the inside roller 61B can be located between the outside roller 65C and the outside roller 65D, and the inside roller 61C can be located between the outside roller 65E and the outside roller 65F. Further, the respective outside rollers 65A to 65F have corresponding roller axes P1 to P6.

The respective outside rollers 65A to 65F can freely rotate relative to the cover member 62 and the proximal-side tubular part 36, with the corresponding roller axes P1 to P6 being the center. Furthermore, the outside rollers 65A to 65F can freely rotate integrally with the rotating unit 30 around the longitudinal axis X relative to the insertion portion 3, or the base part 27.

Due to this configuration, the rotating tubular member 58 can rotate around the longitudinal axis X when the driving force transmitting unit 53 is driven by a rotational driving force. This causes the inside roller 61A to press the outside roller 65A or the outside roller 65B. Similarly, the inside roller 61B is caused to press the outside roller 65C or the outside roller 65D and the inside roller 61C is caused to press the outside roller 65E or the outside roller 65F.

Due to this, the driving force can be transmitted from the inside rollers 61A to 61C to the outside rollers 65A to 65F of the rotating unit 30 and the rotating unit 30 can rotate around the longitudinal axis X relative to the insertion portion 3 and the cover member 62.

As described above, the outside rollers 65A to 65F attached to the proximal-side tubular part 36 form a driving force receiving part that receives the rotational driving force from the driving force transmitting unit 53 that is driven.

The outside rollers 65A to 65F, which are the driving force receiving part, are provided on the proximal direction side relative to the spiral tube 31. Furthermore, in the state in which the rotating unit 30 is mounted to the insertion portion 3, the outside rollers 65A to 65F are located on the outer surface direction side of the base part 27.

Because the respective inside rollers 61A to 61C rotate, with the corresponding roller axes Q1 to Q3 being the center, the friction between the respective inside rollers 61A to 61C and the cover member 62 can be reduced.

Similarly, because the respective outside rollers 65A to 65F rotate, with the corresponding roller axes P1 to P6 being the center, the friction between the respective outside rollers 65A to 65F and the cover member 62 can be reduced.

As depicted in FIG. 8, the cover member 62 can, according to one aspect of the present invention, include a base layer 62B. The base layer 62 can be formed (e.g., molded) of a material, including an elastomer selected for its elastic properties, into a desired shape (e.g., the tubular shape of the cover member 62). Examples of the elastomer forming the base layer 62B can include polyisoprene or natural rubber, polybutadience, polyisobutylene, and polyurethane.

The cover member 62 can further include an outer coating layer 62A formed on an outer surface direction side of the base layer 62B, an inner coating layer 62C formed on an inner surface direction side of the base layer 62B, or both.

A thickness of each of the outer coating layer 62A and the inner coating layer 62C is selected so as to not interfere with or restrict the cover member 62 and in particular the base layer 62B from protruding in the outer surface direction at the sites at which the inside rollers 61A to 61C are located.

The material for forming the outer coating layer 62A and the inner coating layer 62C can be selected to form a durable and chemically resistant coating with good barrier properties for inorganic and organic fluids, strong acids, caustic solutions, gases and water vapors.

The material for forming the outer coating layer 62A is further selected to reduce the coefficient of friction between the outer surface direction side of the cover member 62 and the outside rollers 65A to 65F, as compared to a configuration where the base layer 62B directly contacts the outside rollers 65A to 65F. Similarly, the material for forming the inner coating layer 62C is further selected to reduce the coefficient of friction between the inner surface side of the cover member 62 and the inside rollers 61A to 61C, as compared to a configuration where the base layer 62B directly contacts the inside rollers 61A to 61C.

The material for forming the outer coating layer 62A and the inner coating layer 62C is not particularly limited, but can include material such as silver, ceramic or chemical vapor deposited poly(p-xylylene) polymers (e.g., Parylene), or the like.

Taking the example of Parylene as the material selected for the outer coating layer 62A and the inner coating layer 62C, the Parylene coating can be applied to the outer surface of the base layer 62B and in particular the outer surface side and the inner surface side of the base layer 62B via vapor deposition. The vapor deposition process allows for the Parylene to conformally coat the base layer 62B with a generally consistent thickness without any pinholes or other types of discontinuities.

The Parylene coating can be applied to have a thickness that allows the outer coating layer 62A and the inner coating layer 62C to adhere to the base layer 62B and to remain flexible such that the elongation of the base layer 62B to protrude in the outer surface direction at the sites at which the inside rollers 61A to 61C are located can still be performed to rotate the rotating unit 30. In one embodiment, the Parylene coating can be applied to have a thickness ranging from 0.5 µm to 1.0 µm to maintain adhesion and flexibility to the base layer 62B. The thickness of the Parylene coating is not limited to 0.5 µm to 1.0 µm. Other thickness ranges that allow for adhesion to the base layer 62B and for flexibility at the sites at which the inside rollers 61A to 61C are located are contemplated to be within the scope of the present invention.

Further, the Parylene coating can be applied to have a thickness to be chemically resistant to fluids applied to the insertion portion 3 during reprocessing of the endoscope 2.

Further, the Parylene coating can provide a biocompatible and biostable coating to the surface of the base layer 62B and to provide dry-film lubricity that reduces a coefficient of friction between the outer surface direction side of the cover member 62 and the outside rollers 65A to 65F and between the inner surface direction side of the cover member 62 and the inside rollers 61A to 61C.

Further, the Parylene coating can protect the base layer 62B from oils, dirt and other contamination, while reducing adverse effects, such as flaking or dusting of the elastomeric surface of the base layer 62B.

Further, the Parylene coating can protect the base layer 62B from damage during a cleaning, disinfection and sterilization process of the insertion portion 3 of the endoscope 2 that may involve one or more of exposure to high temperatures and various liquid solutions.

Further, the Parylene coating can be substantially transparent to allow for a color of the base layer 62B or a change in the color of the base layer 62B (as described in more detail below) to be visually inspected.

As depicted in FIG. 9, the cover member 62 can be formed of a mixture or blend of materials including an elastomer, as a base material 62B0, and one or more secondary materials (or additives) that change color in response to temperature change of the one or more secondary materials from a first temperature (or a first temperature range) to a second temperature (or a second temperature range). The change in color can provide an indication of the temperature of the base material 62B0 in thermal contact with the one or more secondary materials.

As an example, the one or more secondary materials can be in the form of thermochromic/thermochromatic liquid crystals or a powder that is mixed with the base material 62B0. The mixture of the base material 62B0 and the one or more secondary materials can then be molded into a desired shape (e.g., the tubular shape of the cover member 621.

Each of the one or more secondary materials can be selected to reversibly change (i.e., color-to-clear change) from a color (that is different from the color of the base material 62B0) to become transparent (or substantially transparent) in response to the temperature of the base material 62B0 exceeding a threshold value or in response to the temperature of the base material 62B0 being within a predetermined temperature range.

Further, each of the one or more secondary materials can be selected to reversibly change (i.e., clear-to-color) from being transparent (or substantially transparent) to being of a color (that is different from the color of the base material 62B0) in response to the temperature of the base material 62B0 exceeding a threshold value or in response to the temperature of the base material 62B0 being within a predetermined temperature range.

As an example, a secondary material 62B1 of the one or more secondary materials can be selected to reversibly make a color-to-clear change in response to being heated from a first temperature associated with a first temperature of the base material 62B0 having a higher coefficient of friction to a second temperature associated with a second temperature of the base material 62B0 having a lower coefficient of friction, where the second temperature of the base material 62B0 is higher than the first temperature of the base material 62B0.

As an example, the secondary material 62B1 of the one or more secondary materials can be selected to reversibly make a clear-to-color change in response to being heated from the first temperature associated with the first temperature of the base material 62B0 having the higher coefficient of friction to the second temperature associated with the second temperature of the base material 62B0 having the lower coefficient of friction, where the second temperature of the base material 62B0 is higher than the first temperature of the base material 62B0.

Here, the second temperature of the base material 62B0 having the lower coefficient of friction can be a body temperature (e.g., 37 degrees Celsius) or a body temperature range (e.g., 36.5 to 37.5 degrees Celsius).

As another example, a secondary material 62B2 of the one or more secondary materials can be selected to reversibly make a color-to-clear change in response to being heated from a first temperature associated with a room temperature or a storage temperature of the base material 62B0 to a second temperature associated with a second temperature of the base material 62B0 during reprocessing of the insertion portion 3 of the endoscope 2 that would successfully clean, disinfect and sterilize the insertion portion 3 of the endoscope 2.

As another example, the secondary material 62B2 of the one or more secondary materials can be selected to reversibly make a clear-to-color change in response to being heated from the first temperature associated with the room temperature or the storage temperature of the base material 62B0 to the second temperature associated with the second temperature of the base material 62B0 during reprocessing of the insertion portion 3 of the endoscope 2 that would successfully clean, disinfect and sterilize the insertion portion 3 of the endoscope 2.

As yet another example, a secondary material 62B3 of the one or more secondary materials can be selected to reversibly make a color-to-clear change in response to being heated or cooled from a first temperature associated with the room temperature or the storage temperature of the base material 62B0 to a second temperature associated with an original manufacturer of the endo scope 2.

As yet another example, the secondary material 62B3 of the one or more secondary materials can be selected to reversibly make a clear-to-color change in response to being heated or cooled from the first temperature associated with the room temperature or the storage temperature of the base material 62B0 to the second temperature associated with the original manufacturer of the endo scope 2.

As depicted in FIG. 10, in one modification, the one or more secondary materials described above can be applied to the base material 62B0 by spray coating, dip coating, or the like instead of being formed as a mixture with the base material 62B0.

As depicted in FIG. 11, in another modification, the base layer 62B, formed as a mixture of base material 62B0 and the one or more secondary materials, or as the base material 62B0 coated by the one or more secondary materials, can be further provided with the outer coating layer 62A. As described above, by forming the outer coating layer 62A from a substantially transparent material such as the Parylene coating, the color-to-clear change or the clear-to-color change of the one or more secondary materials can be visually inspected through the outer coating layer 62A.

Based on the above-described structure of the cover member 62 and the relative arrangement of the cover member 62 with the inside rollers 61A to 61C and the outside rollers 65A to 65F, the rotational driving force can be properly transmitted from the inside rollers 61A to 61C to the rotating unit 30 to rotate the rotating unit 30.

In the proximal-side tubular part 36, a locking claw 67 that protrudes in the inner surface direction is provided. Furthermore, in the support member 51 of the base part 27, a locking groove 68 can be provided across the whole circumference regarding the direction around the longitudinal axis.

The locking claw 67 can be locked to the locking groove 68 and thereby movement of the rotating unit 30 along the longitudinal axis X relative to the insertion portion 3 can be regulated. However, in the state in which the locking claw 67 is locked to the locking groove 68, the locking claw 67 can freely move in the direction around the longitudinal axis relative to the locking groove 68.

As depicted in FIG. 2 and FIG. 4, a guide tube 77 can be extended along the longitudinal axis X inside the third flexible tube part 26 of the insertion portion 3. The distal end of the guide tube 77 can be connected to the support member 51 of the base part 27.

A guide channel 78 can be formed inside the guide tube 77. The distal end of the guide channel 78 can communicate with the hollow part 52. In the guide channel 78, a drive shaft 79 that is a linear part can be extended along a shaft axis S.

The rotational driving force generated by the electric motor 72 is transmitted to the drive shaft 79 via the relay gear 75 and the drive gear 76. Due to the transmission of the rotational driving force to the drive shaft 79, the drive shaft 79 rotates around the shaft axis S.

The distal end of the drive shaft 79 can be connected to the drive gear 55 of the driving force transmitting unit 53. Due to the rotation of the drive shaft 79, the rotational driving force can be transmitted to the driving force transmitting unit 53 and the driving force transmitting unit 53 can be driven. Then, the rotational driving force can be transmitted to the rotating tubular member 58 and thereby the rotational driving force can be transmitted to the rotating unit 30 as described above to rotate the rotating unit 30.

As depicted in FIG. 5, bending wires 38A and 38B can be extended along the longitudinal axis X inside the insertion portion 3. The proximal ends of the bending wires 38A and 38B can be connected to a pulley (not depicted) joined to the bending operation knob 37 inside the operation unit 5.

The distal ends of the bending wires 38A and 38B can be connected to the distal part of the bending part 22. By performing the bending operation with the bending operation knob 37, the bending wire 38A or the bending wire 38B can be pulled and the bending part 22 bends. In the present embodiment, the bending part 22 can be formed of only an active bending part that bends by bending operation.

The respective bending wires 38A and 38B can be inserted in corresponding coils 39A and 39B. The proximal ends of the coils 39A and 39B can extend to the inside of the operation unit 5. Furthermore, the distal ends of the coils 39A and 39B can be connected to the inner circumferential surface of the distal part of the first flexible tube part 23. In the present embodiment, the two bending wires 38A and 38B are provided and the bending part 22 can bend in two directions. However, for example, four bending wires can be provided and the bending part 22 can bend in four directions.

Figure 6:
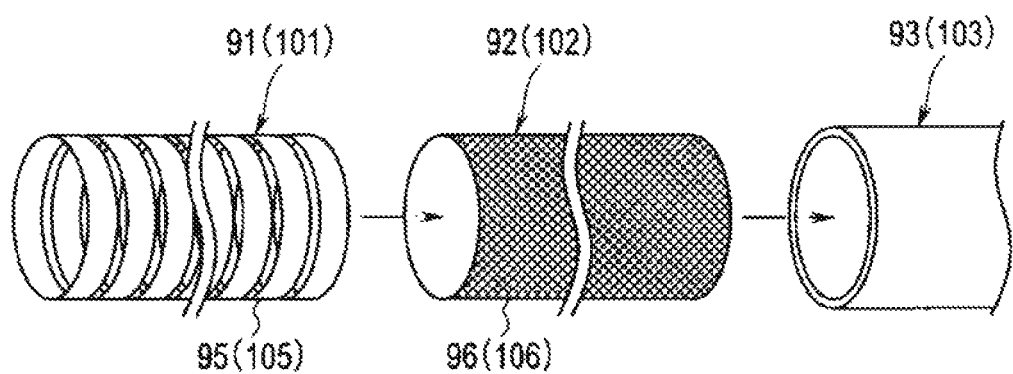
FIG. 6 is an exploded perspective view in which the first flexible tube part and the second flexible tube part are disassembled on each member basis according to the one aspect of the present disclosure.
Figure 7:
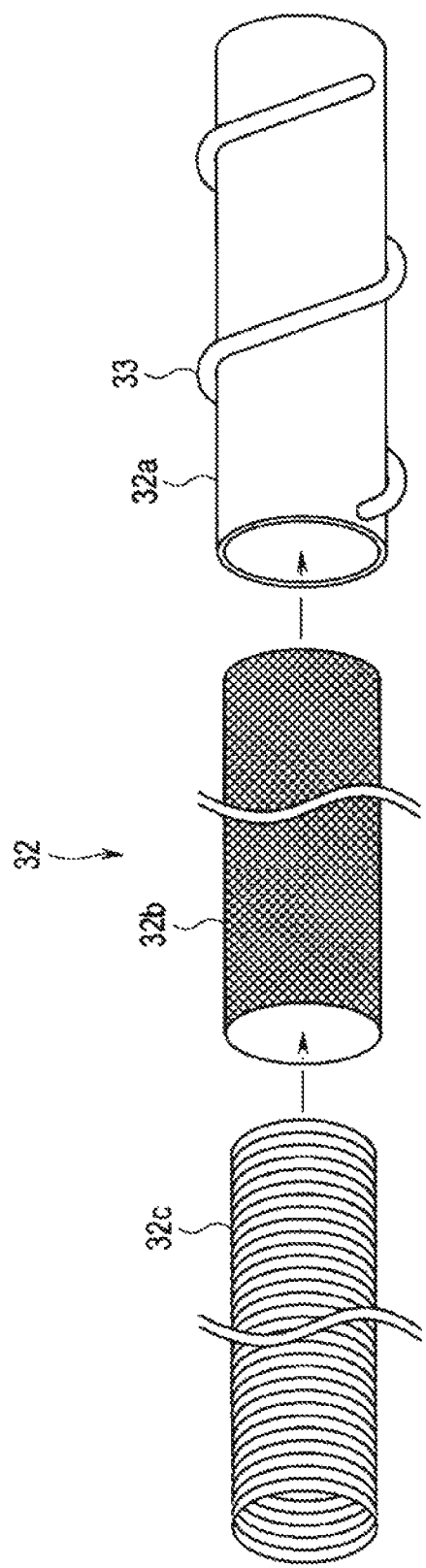
FIG. 7 is an exploded perspective view that depicts a first form of a spiral tube and in which a tube part is disassembled on each member basis according to the one aspect of the present disclosure.

As depicted in FIG. 6, the first flexible tube part 23 and the second flexible tube part 25 are formed of a first helical tube 91 that is a first flex tube, a first flexible reticular tube 92 that is a first flexible blade tube, and a first flexible envelope 93 that is an envelope tube.

The first helical tube 91, the first flexible reticular tube 92, and the first flexible envelope 93 can be extended along the longitudinal axis X from the distal end of the first flexible tube part 23 to the proximal end of the second flexible tube part 25.

The outer surface direction side of the first helical tube 91 can be covered by the first flexible reticular tube 92 and the outer surface direction side of the first flexible reticular tube 92 can be covered by the first flexible envelope 93.

The first helical tube 91 can include a strip-shaped member 95 made of a metal. In the first helical tube 91, the strip-shaped member 95 can extend into a helical shape around the longitudinal axis X. The first flexible reticular tube 92 can include wires 96 made of a metal. The wires 96 can be woven in the first flexible reticular tube 92. The first flexible envelope 93 can be formed of a resin material for example.

The proximal part of the bending tube 81 can be fitted to a connecting tube 84 with a tubular shape (see FIG. 3) and the first helical tube 91 and the first flexible reticular tube 92 can be fitted to the connecting tube 84 in the state of being inserted on the inner surface direction side of the connecting tube 84.

Furthermore, the first flexible envelope 93 can be bonded to the bending envelope 85 with the intermediary of a bonding part 86 such as an adhesive. The first flexible tube part 23 can be joined to the bending part 22 in the above-described manner. As depicted in FIG. 4, the first helical tube 91, the first flexible reticular tube 92, and the first flexible envelope 93 can be fitted to the support member 51 in the state of being inserted on the inner surface direction side of the support member 51.

Thereby, the second flexible tube part 25 can be joined to the base part 27. Furthermore, in the present embodiment, the first helical tube 91, the first flexible reticular tube 92, and the first flexible envelope 93 can be extended in a continuous state between the first flexible tube part 23 and the second flexible tube part 25.

The third flexible tube part 26 can be formed of a second helical tube 101 that is a second flex tube, a second flexible reticular tube 102 that is a second flexible blade tube, and a second flexible envelope 103 (reference numerals in parentheses in FIG. 6).

The second helical tube 101, the second flexible reticular tube 102, and the second flexible envelope 103 can extend along the longitudinal axis X from the distal end of the third flexible tube part 26 to the proximal end of the third flexible tube part 26. The outer surface direction side of the second helical tube 101 is covered by the second flexible reticular tube 102 and the outer surface direction side of the second flexible reticular tube 102 is covered by the second flexible envelope 103.

The proximal end of the support member 51 can be fitted to a connecting member 104. The second helical tube 101 and the second flexible reticular tube 102 can be fitted to the connecting member 104 in the state of being inserted on the inner surface direction side of the connecting member 104 (see FIG. 4). Due to this, the third flexible tube part 26 can be joined to the base part 27.

In the second helical tube 101, a strip-shaped member 105 made of a metal can be extended into a helical shape centered at the longitudinal axis X. Furthermore, in the second flexible reticular tube 102, wires 106 made of a metal are woven. The second flexible envelope 103 can be formed of a resin material, for example.

Referring back to the description of the color-to-clear and clear-to-color change of the cover member 62, it is also within the scope of the present invention for the one or more secondary materials to be provided to other portions of the insertion portion 3. For example, the one or more secondary materials can also be provided to one or more of the bending envelope 85, the first flexible envelope 93, and the second flexible envelope 103.

As an example, the one or more secondary materials can be provided in a mixture with the fluorine rubber that is a base material for the bending envelope 85 or coated to the surface of the base material for the bending envelope 85.

As another example, the one or more secondary materials can be provided in a mixture with the resin material that is a base material for the first flexible envelope 93 or coated to the surface of the base material for the first flexible envelope 93.

As yet another example, the one or more secondary materials can be provided in a mixture with the resin material that is a base material for the second flexible envelope 103 or coated to the surface of the base material for the second flexible envelope 103.

In another embodiment of the invention, there is provided a method of processing the endoscope apparatus 1 described above.

Figure 12:
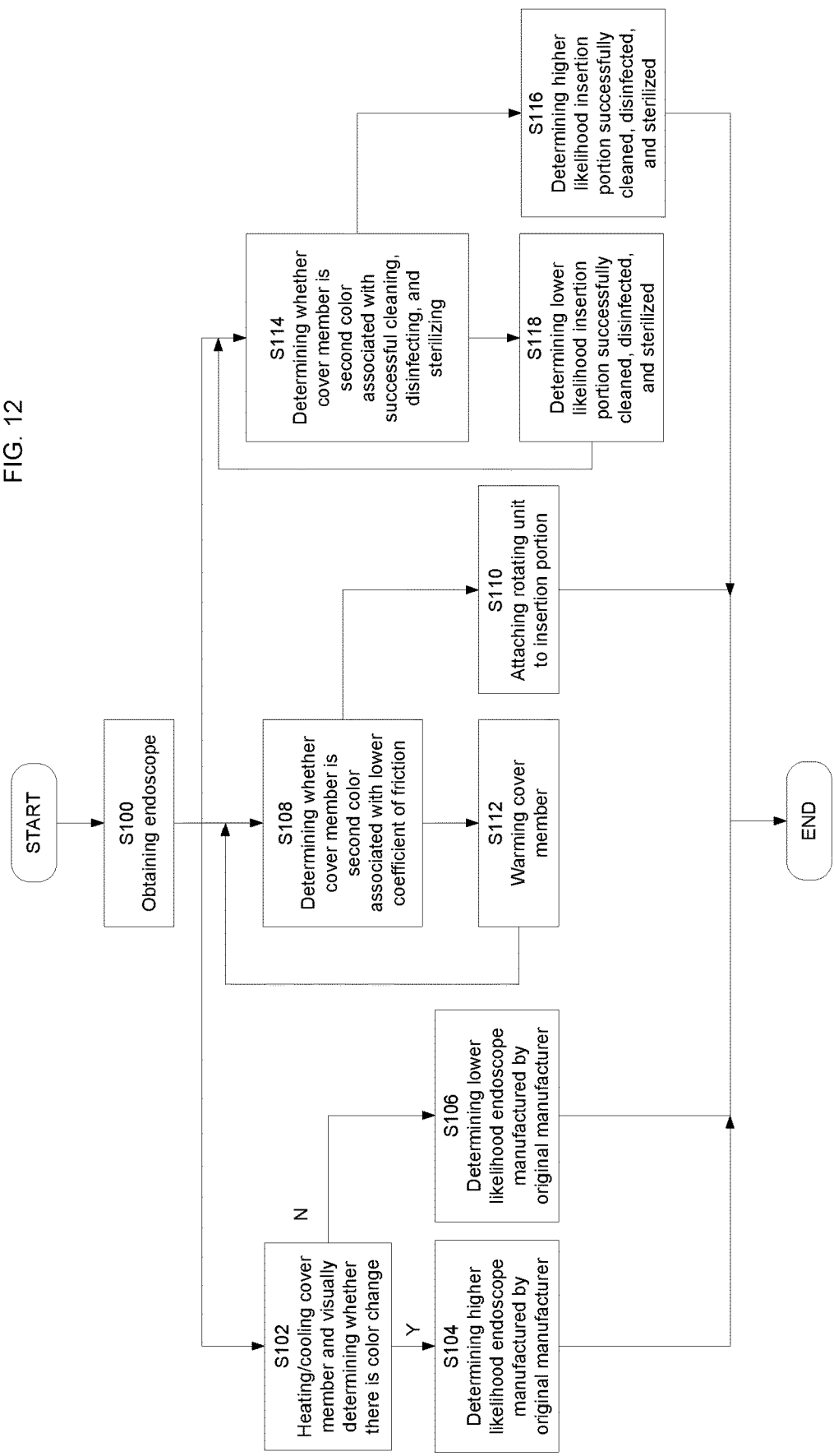
FIG. 12 is a flowchart showing a method of processing the endoscope apparatus according to one aspect of the present disclosure.

As depicted in FIG. 12, the method can begin with a step S100 of obtaining the endoscope 2. Following step S100, the method can further include a step S102 of heating or cooling the cover member 62, and in particular, the secondary material 62B3 of the cover member 62, to the second temperature associated with the original manufacture of the endoscope 2, and visually inspecting the cover member 62 to determine whether the cover member 62 undergoes a change in visual appearance (e.g., color-to-clear change or a clear-to-color change), as described above.

In response to determining that the cover member 62 undergoes the color-to-clear change or the clear-to-color change, as described above, it is further determined at a step S104 that there is a higher likelihood that the endoscope 2 was manufactured by the original manufacturer.

In contrast, in response to determining that the cover member 62 does not undergo the color-to-clear change or the clear-to-color change, as described above, it is further determined at a step S106 that there is a lower likelihood that the endoscope 2 was manufactured by the original manufacturer (or that there is a higher likelihood that the endoscope 2 or parts of the endoscope 2 was manufactured by a third party different from the original manufacturer).

Following the step S100, the method can further include a step S108 of visually inspecting the cover member 62 to determine whether the secondary material 62B1 of the cover member 62 has undergone the color-to-clear change or the clear-to-color change to the second color associated with the second temperature of the base material 62B0 having the lower coefficient of friction.

In response to determining that the secondary material 62B1 of the cover member 62 has undergone the color-to-clear change or the clear-to-color change to the second temperature associated with the second temperature of the base material 62B0 having the lower coefficient of friction, the method can further include a step S110 of attaching the rotating unit 30 to the insertion portion 3 such that the rotational driving force from the driving force transmitting unit 53 can be transmitted to the rotating unit 30 to rotate the rotating unit 30.

In response to determining that the secondary material 62B1 of the cover member 62 has not undergone the color-to-clear change or the clear-to-color change to the second temperature associated with the second temperature of the base material 62B0 having the lower coefficient of friction, the method can further include a step S112 of warming the cover member 62. Warming of the cover member 62 can be achieved by, for example, physical contact with a warmer surface such as the hand of a technician or by a warming device such as a hot water bath. Following the step S112, the method can return to the step S108 of visually inspecting the cover member 62 to determine whether the secondary material 62B1 of the cover member 62 has undergone the color-to-clear change or the clear-to-color change to the second temperature associated with the second temperature of the base material 62B0 having the lower coefficient of friction.

Following the step S100, the method can further include a step S114 of reprocessing the insertion portion 3 of the endoscope 2. The reprocessing of the insertion portion 3 can include one or more of cleaning, disinfecting and sterilizing the insertion portion 3 at a predetermined temperature that is higher than the room temperature or the storage temperature of the base material 62B0.

During (or immediately following) the step S114, the method can further include a step of visually inspecting the cover member 62 to determine whether the secondary material 62B1 of the cover member 62 has undergone the color-to-clear change or the clear-to-color change to the second color associated with successfully cleaning, disinfecting and sterilizing the insertion portion 3 of the endoscope 2.

In response to determining that the secondary material 62B1 of the cover member 62 has undergone the color-to-clear change or the clear-to-color change to the second temperature associated with successfully cleaning, disinfecting and sterilizing the insertion portion 3 of the endoscope 2, it is further determined at a step S116 that there is a higher likelihood that the insertion portion 3 of the endoscope 2 was successfully cleaned, disinfected and sterilized.

If the one or more of the secondary materials are also provided to other portions of the insertion portion 3 such as the bending envelope 85, the first flexible envelope 93, and the second flexible envelope 103, a visual inspection of the insertion portion 3 can be made to ascertain whether there is a higher likelihood that the other portions of the insertion portion 3 were successfully cleaned, disinfected and sterilized.

In response to determining that the secondary material 62B1 of the cover member 62 has not undergone the color-to-clear change or the clear-to-color change to the second color associated with successfully cleaning, disinfecting and sterilizing the insertion portion 3 of the endoscope 2, it is further determined at a step S118 that there is a lower likelihood that the insertion portion 3 of the endoscope 2 was successfully cleaned, disinfected and sterilized. The method can return to the step S114 of reprocessing the insertion portion 3 of the endoscope 2.

Those of ordinary skill in the art may recognize that many modifications and variations of the disclosed apparatus and method may be implemented without departing from the spirit or scope of the invention. Thus, it is intended that the present invention covers such modifications and variations provided they come within the scope of the appended claims and their equivalents.

What is claimed is:

1. An endoscope apparatus comprising:
an insertion portion extending along a longitudinal axis;
a roller configured to be driven by a drive force to rotate around the longitudinal axis of the insertion portion; and
a cover member configured to be attached to the insertion portion to cover the roller, wherein the cover member comprises:
a base layer having:
an outer surface direction side; and
an inner surface direction side arranged to contact the roller, wherein portions of the base layer covering the roller as the roller rotates around the longitudinal axis of the insertion portion are configured to be elastically elongated in an outer surface direction of the insertion portion, and wherein the base layer comprises:
an elastomer; and
one or more secondary materials configured to change color in response to temperature change of the one or more secondary materials; and an external coating layer formed on at least one of the outer surface direction side and the inner surface direction side of the base layer, wherein the external coating layer comprises a material selected to reduce a coefficient of friction of an outer surface of the cover member as compared to a coefficient of friction of the base layer and the roller.

2. The endoscope apparatus according to claim 1, comprising:
an assist tool comprising:
a tubular part configured to engage the roller via the external coating layer and the portions of the base layer elastically elongated by the roller to thereby receive the drive force and be rotated by the drive force with respect to the insertion portion.

3. The endoscope apparatus according to claim 1, wherein the external coating layer comprises silver.

4. The endoscope apparatus according to claim 1, wherein the external coating layer comprises a chemical vapor deposited poly(p-xylylene) polymer.

5. The endoscope apparatus according to claim 1, wherein the one or more secondary materials is configured to be of a first color at a first temperature range and to be of a second color at a second temperature range.

6. The endoscope apparatus according to claim 5, wherein a predetermined coefficient of friction of the base layer corresponds to the second temperature range of the one or more secondary materials.

7. A method of processing an endoscope apparatus, wherein the endoscope apparatus comprises:
an insertion portion extending along a longitudinal axis;
a roller configured to be driven by a drive force to rotate around the longitudinal axis of the insertion portion; and
a cover member configured to be attached to the insertion portion to cover the roller, wherein the cover member comprises:
a base layer,
wherein portions of the base layer covering the roller as the roller rotates around the longitudinal axis of the insertion portion are configured to be elastically elongated in an outer surface direction of the insertion portion, and
wherein the base layer comprises:
an elastomer; and
a secondary material configured to change color in response to temperature change of the secondary material from a first temperature associated with a first temperature of the elastomer having a higher coefficient of friction to a second temperature associated with a second temperature of the elastomer having a lower coefficient of friction, and wherein the method comprises:
performing inspection of the cover member to determine whether the secondary material has undergone the change in color;
in response to determining that the secondary material has not undergone the change in color, performing warming the cover member;
repeating performance of the inspection of the cover member and the warming of the cover member until determining that the secondary material has undergone the change in color; and
in response to determining that the secondary material has undergone the change in color, attaching an assist tool having a tubular shape to the insertion portion at a position where the drive force is transmitted from the roller to the rotating unit via the cover member.

8. An endoscope apparatus comprising:
an insertion portion extending along a longitudinal axis;
a roller configured to be driven by a drive force to rotate around the longitudinal axis of the insertion portion; and
a cover member configured to be attached to the insertion portion to cover the roller, wherein the cover member comprises:
a base layer having:
an outer surface direction side; and
an inner surface direction side arranged to contact the roller,
wherein portions of the base layer covering the roller as the roller rotates around the longitudinal axis of the insertion portion are configured to be elastically elongated in an outer surface direction of the insertion portion, and
wherein the base layer comprises:
an elastomer; and
one or more secondary materials configured to change color in response to temperature change of the one or more secondary materials; and
an external coating layer formed on at least one of the outer surface direction side and the inner surface direction side of the base layer.

9. The endoscope apparatus according to claim 8, wherein the one or more secondary materials is configured to be of a first color at a first temperature range and to be of a second color at a second temperature range.

10. The endoscope apparatus according to claim 9, wherein a predetermined coefficient of friction of the base layer corresponds to the second temperature range of the one or more secondary materials.

11. A method of operating an endoscope apparatus, wherein the endoscope apparatus comprises:
an insertion portion extending along a longitudinal axis;
a roller configured to be driven by a drive force to rotate around the longitudinal axis of the insertion portion; and
a cover member configured to be attached to the insertion portion to cover the roller, wherein the cover member comprises:
a base layer having:
an outer surface direction side; and
an inner surface direction side arranged to contact the roller,
wherein portions of the base layer covering the roller as the roller rotates around the longitudinal axis of the insertion portion are configured to be elastically elongated in an outer surface direction of the insertion portion, and
wherein the base layer comprises:
an elastomer; and
one or more secondary materials configured to change color in response to temperature change of the one or more secondary materials; and
an external coating layer formed on at least one of the outer surface direction side and the inner surface direction side of the base layer,
wherein the external coating layer comprises a material selected to reduce a coefficient of friction of an outer surface of the cover member as compared to a coefficient of friction of the base layer and the roller,
wherein the method comprises:
performing inspection of the cover member to determine whether the secondary material has undergone the change in color;
in response to determining that the secondary material has not undergone the change in color, performing warming the cover member;
repeating performance of the inspection of the cover member and the warming of the cover member until determining that the secondary material has undergone the change in color:
providing the drive force; and
driving, by the drive force, the roller to rotate around the longitudinal axis of the insertion portion while covered by the cover member, wherein the material of the external coating layer of the cover member reduces a coefficient of friction of the outer surface of the cover member as compared to a coefficient of friction of the base layer and the roller.

12. The method according to claim 11, further comprising:
providing an assist tool comprising a tubular part to engage the tubular part to the roller via the external coating layer and the portions of the base layer elastically elongated by the roller to thereby receive the drive force and be rotated by the drive force with respect to the insertion portion.

* * * * *